United States Patent [19]

Lucas et al.

[11] 4,410,442

[45] Oct. 18, 1983

[54] DISINFECTING SOLUTIONS FOR HYDROPHILIC CONTACT LENSES

[75] Inventors: Donald S. Lucas; Robert V. Mustacich; Roger L. Stone, all of Fairfield, Ohio

[73] Assignee: The Procter & Gamble Company, Cincinnati, Ohio

[21] Appl. No.: 339,218

[22] Filed: Jan. 13, 1982

[51] Int. Cl.$^3$ ............................................. C11D 9/50
[52] U.S. Cl. ................................. 252/107; 252/106; 424/317; 424/318
[58] Field of Search ................ 252/106, 107; 424/317, 424/318

[56] References Cited

U.S. PATENT DOCUMENTS

| Re. 29,693 | 7/1978 | Phares, Jr. | 424/326 |
|---|---|---|---|
| 2,466,663 | 4/1949 | Russ | 167/28 |
| 2,841,526 | 7/1958 | Gustus | 424/317 |
| 3,171,752 | 3/1965 | Rankin | 106/194 |
| 3,743,519 | 7/1973 | Haas | 99/159 |
| 4,046,706 | 9/1977 | Krezanoski | 252/106 |
| 4,259,202 | 3/1981 | Tanaka et al. | 252/106 |
| 4,323,467 | 4/1982 | Fu | 252/106 |

FOREIGN PATENT DOCUMENTS 2400906 3/1979 France .
53-28922 8/1978 Japan .

OTHER PUBLICATIONS

"Lipids as Safe and Effective Antimicrobial Agents for Cosmetics and Pharmaceuticals", Jon J. Kabara, Cosmetics and Perfumery, pp. 21-25, vol. 90, May 1975.
Handbook of Nonprescription Drugs, 5th ed., Am. Phar. Asso. 1977, pp. 236-247, Theodore, *JAMA*, 143:226 (1950).
Keeney, *Bull. Johns Hopkins Hosp.* 78:333 (1946).

*Primary Examiner*—John E. Kittle
*Assistant Examiner*—Hoa Van Le
*Attorney, Agent, or Firm*—Steven J. Goldstein; David L. Suter; Jack D. Schaeffer

[57] ABSTRACT

Disinfecting solutions for use with hydrophilic soft contact lenses, containing effective amounts of $C_5$-$C_{12}$ fatty acids, especially octanoic acid, are disclosed. These solutions provide broad spectrum antimicrobial efficacy together with rapid and complete desorption of the fatty acid antimicrobial from the contact lens material, resulting in a minimization of irritation and sensitization risks to the user. The method of disinfecting hydrophilic soft contact lenses using $C_5$-$C_{12}$ fatty acids is also disclosed.

19 Claims, No Drawings

DISINFECTING SOLUTIONS FOR HYDROPHILIC CONTACT LENSES

TECHNICAL FIELD

The present invention relates to aqueous solutions used for the cleaning, disinfecting and storing of hydrophilic soft contact lenses.

BACKGROUND OF THE INVENTION

Hydrophilic or partially hydrophilic plastic materials have been used in making "soft" contact lenses. For example, U.S. Pat. Nos. 3,503,393 and 2,976,576 describe processes for producing three dimensional hydrophilic polymers of polyhydroxyethylmethacrylate in aqueous reaction media; these polymers have low degrees of cross-linking in their hydrogel structure and have the appearance of elastic, soft, transparent hydrogels. Soft contact lenses have also been made out of silicone and other optically suitable flexible materials. The popularity of soft contact lenses is growing rapidly. The major virtues of these lenses are their softness (providing comfort to the wearer), permeability to gases, and their optical suitability. The hydrophilic lenses are particularly useful for ophthalmological applications due to their ability to absorb water with a concomitant swelling to a soft mass of extremely good mechanical strength, their complete transparency, and their ability to retain shape and dimension when equilibrated in a given fluid.

One very basic problem associated with soft contact lenses is the development of a convenient, safe and effective method for disinfecting and cleaning them. The fact that these lenses are hydrophilic (compared with hard contact lenses) makes them a good environment for breeding microbial contamination; this requires that the lenses be well-disinfected prior to each use. The properties of the polymers used in the lenses allows conventional preservatives and antimicrobials, which might otherwise be used for cleaning and disinfecting, to be absorbed annd concentrated in the lenses and later released when the contact lenses are on the eye. The release of such antimicrobial and preservative materials is generally much slower than the uptake, thereby allowing them to build up in the lenses. This buildup may eventually affect the physical characteristics of the lenses, including their dimension and color. The net result of this process can be the damaging or staining of the contact lens, itself, and/or harming the sensitive conjunctival or corneal tissue in the eye.

Hard contact lenses do not absorb appreciable amounts of water (i.e., only from about 0.1 to about 0.4%) and thus the use of conventional preservatives and antimicrobials generally does not present a problem in the hard contact lens field. Disinfecting of soft contact lenses is frequently carried out by boiling the lenses in normal saline, an inconvenient and cumbersome procedure. Furthermore, wearers of soft contact lenses are often warned that solutions designed for hard contact lenses should not be used with soft lenses, since the preservatives in such solutions will be absorbed and even concentrated by the soft lenses and may seriously damage the contact lens and/or the eye of the user.

Thimerosal (sodium ethylmercurithiosalicylate) and chlorhexidine are well-known preservatives, frequently used in contact lens disinfecting solutions. See, for example, *Handbook of Nonprescription Drugs*, 5th ed., American Pharmaceutical Association, 1977, pages 236–247, and U.S. Pat. No. Re. 29,693, Phares, reissued July 4, 1978. The use of certain organic acids as components in contact lens cleaning solutions has been disclosed in the art. Japanese Specification No. 78-28,922, Allergan Pharmaceuticals, issued Aug. 17, 1978, describes contact lens cleaning solutions containing polyoxyethylene stearate. French Pat. No. 2,400,906, issued March 23, 1979, describes the use of ascorbic acid and sodium ascorbate in contact lense cleaning solutions.

$C_5$–$C_{12}$ fatty acids and fatty acid salts are known to be effective antimicrobial and antifungal agents. Keeney, *Bull. Johns Hopkins Hosp.* 78, 333 (1946), teaches the use of a 20% aqueous solution of sodium caprylate, at pH 7.4, to successfully treat moniliasis. U.S. Pat. No. 2,466,663, Russ, et al., issued Apr. 5, 1949, discloses aqueous solutions, having pH's between 4.5 and 10.5, containing a mixture of caprylic acid and a caprylic acid salt, especially zinc or sodium caprylate. These solutions are taught to be useful in preventing the growth of molds or fungi in foods and other nutrient media. Theodore, *JAMA* 143, 226(1950), discloses that the lower fatty acids have been shown to be of value in the treatment of external infections of the eyes. Specifically, sodium propionate was found effective against bacteria causing common occular and fungal infections, including staphylococcus and *Pseudomonas aeruginosa*. Copending U.S. patent application Ser. No. 918,532, Stone, filed June 23, 1978, describes the use of octanoic acid as a broad spectrum antimicrobial agent in intravenous, nutrient and dialysis solutions; these solutions typically contain electrolytes, such as sodium chloride. The antimicrobial benefits of maintaining a solution pH between about 3.5 and 6.0 are taught.

It has now been discovered that when the $C_5$–$C_{12}$ fatty acids are used in disinfecting solutions (also referred to as sterilization solutions in the art) for soft contact lenses, these solutions provide broad spectrum antimicrobial activity, compatibility with the hydrophilic soft contact lens material, and very rapid and complete desorption of the antimicrobial agent from the contact lens material, thereby minimizing the eye irritation and sensitization problems discussed above.

It is, therefore, an object of the present invention to provide an effective cleaning, disinfecting and storing solution for soft contact lenses characterized by rapid and complete desorption of the antimicrobial material from the lens.

It is a further object of the present invention to formulate aqueous solutions suitable for cleaning, disinfecting and storing hydrophilic soft contact lenses containing $C_5$–$C_{12}$ fatty acids.

It is a still further object of the present invention to provide a method for cleaning and disinfecting hydrophilic soft contact lenses utilizing $C_5$–$C_{12}$ fatty acids.

SUMMARY OF THE INVENTION

The present invention relates to aqueous isotonic solutions having a pH between about 3.5 and 6.5, suitable for cleaning, disinfecting and storing hydrophilic soft contact lenses, comprising:

(a) from about 0.001% to about 3% of a $C_5$–$C_{12}$ fatty acid, especially octanoic acid;

(b) a sufficient amount of at least one water-soluble salt, compatible with ocular tissue, to provide a solution salt content equivalent to from about 0.5% to about 1.8% sodium chloride;

(c) from about 0.01% to about 2% of a calcium chelator, especially ethylenediamine tetraacetic acid and its pharmaceutically-acceptable salts; and (d) the balance water.

The present invention also encompasses a method for cleaning and disinfecting hydrophilic soft contact lenses wherein said lenses are contacted with an effective amount of a $C_5$–$C_{12}$ fatty acid, especially octanoic acid.

DETAILED DESCRIPTION OF THE INVENTION

The compositions of the present invention are formulated as aqueous isotonic solutions which contain three basic components: (1) a $C_5$–$C_{12}$ fatty acid or a mixture of such acids; (2) a water-soluble, ocular tissue-compatible salt; and (3) a calcium chelator. These components are dissolved in water which has been prepared in such a way so as to be compatible for use in the eye (e.g., pyrogen-free water). When formulated and used as described herein, the solutions of the present invention provide the following advantages over the currently-used soft contact lens disinfecting solutions: (1) rapid and broad spectrum cidal activity; (2) rapid and complete desorption of the antimicrobial agent from the contact lens material, thereby minimizing eye sensitization and irritation problems; and (3) usage flexibility, since the solutions of the present invention may be used interchangeably in both hot and cold sterilization procedures without causing the lenses to turn opaque.

The phrase "safe and effective amount", as used herein, means sufficient fatty acid component, comprising at least the minimum lethal concentration in aqueous solution of the free acid form of the particular fatty acid being used, to provide the desired antimicrobial benefit in the context of and under the conditions utilized in the soaking and disinfecting of hydrophilic soft contact lenses, not to exceed an amount which is compatible with the compositions herein and safe for use in conjunction with ocular tissue.

"Pharmaceutically-acceptable" or "pharmacologically-acceptable", as used herein, means that the fatty acid compound and other ingredients used in the compositions are suitable for use in contact with the tissue of humans, particularly ocular tissue, without undue toxicity, irritation, allergic response, and the like, commensurate with a reasonable benefit/risk ratio.

The term "comprising", as used herein, means that various other compatible components, including both active and inert ingredients, can be conjointly employed in the compositions of this invention, as long as the critical fatty acid compounds are used in the manner disclosed. The term "comprising" thus encompasses and includes the more restrictive terms "consisting of" and "consisting essentially of".

By "compatible" herein is meant that the components of the present invention are capable of being commingled without interacting in a manner which would substantially decrease the efficacy of the fatty acids under ordinary use conditions.

All percentages and ratios used herein are by weight, unless otherwise specified.

The fatty acids useful in the present invention include those having from about 5 to about 12 carbon atoms; carboxylic acids outside of this range are significantly less effective as antimicrobial agents. These materials, themselves, are well-known in the art. For example, octanoic acid is an oily liquid having a boiling point of 239.7° C. and a melting point of 16.7° C.; it is very slightly soluble in water (0.068 grams/100 grams at 20° C.) and freely soluble in alcohol, chloroform, carbon disulfide, petroleum ether and glacial acetic acid. Octanoic acid may be prepared from 1-heptene, Dupont, et al., *Compt. Rend.* 240, 628 (1955), or by the oxidation of octanol, Langenbeck, et al., *Ber.*, 89, 202 (1956). The manufacture of octanoic acid is described in U.S. Pat. No. 2,821,532, issued in 1958 and assigned to GAF, and U.S. Pat. No. 3,053,869, issued in 1960 and assigned to Standard Oil of Indiana. See also *Fatty Acids*, part 1, K. S. Merkley, Editor (Interscience, New York, 2nd Ed., 1960) pages 34–38. Decanoic acid is a crystalline solid having a melting point of 31.4° C.; it is practically insoluble in water. See *Fatty Acids*, part 1, supra, pages 34–39. Decanoic acid may be prepared from octylbromide, Shishido, et al., *J. Am. Chem. Soc.* 81, 5817 (1959), and U.S. Pat. No. 2,918,494, issued in 1959 and assigned to Ethyl Corp.

It is preferred that the fatty acid component used in the present invention be a $C_5$–$C_{12}$ non-aromatic carboxylic acid, such as n-pentanoic, n-hexanoic, n-heptanoic, n-octanoic, n-nonanoic, n-decanoic, n-undecanoic, or n-dodecanonic acid. Preferred fatty acid materials for use in the present invention contain from 6 to 10 carbon atoms, with octanoic and decanoic acid being particularly preferred. Mixtures of the above fatty acid materials may also be used, as may salts of the fatty acids, provided that the pH criteria for the compositions, as described below, are met.

The compositions of the present invention contain from about 0.001% to about 3%, preferably from about 0.01% to about 1.5% of the fatty acid materials. The compositions are formulated to have a pH of no greater than about 6.5 and no less than about 3.5, preferably the pH falls between about 5 and about 6.5. At pH's above this range, the antimicrobial performance of the composition falls off significantly; obviously a pH which is too low (acidic) would not be suitable for use in an ocular context. Compatible acidic or basic ingredients may be used to adjust the pH of the compositions to the desired range.

The solutions of the present invention must also contain at least one water-soluble salt, compatible with ocular tissue, sufficient in amount to provide a solution salt content equivalent to from about 0.5% to about 1.8% sodium chloride. The purpose of this water-soluble salt is to make the solution isotonic. Hypotonic solutions (for example, tap water) will cause the contact lens to adhere too tightly to the cornea, while a hypertonic solution (for example, excess saline) will result in stinging, lacrimation and red eyes. Mixtures of water-soluble salts may be used as long as the isotonicity of the solution is maintained. Examples of water-soluble salts useful in the present invention include sodium chloride, sodium citrate, sodium lactate, sodium phosphate, the sodium salts of the fatty acids defined above (such as sodium octanoate), and mixtures thereof, with sodium chloride being especially preferred.

The compositions of the present invention also contain from about 0.01% to about 2%, preferably from about 0.05% to about 1.5% of a calcium chelator component. This chelating agent is used to prevent metal ions, such as calcium ions, from fixing to the surfaces of the contact lenses and for removing those metal ions which are fixed to the surfaces of the lenses. Buildup of calcium ions on the lenses may cause eye irritation. Useful chelating agents include aminopolycarboxylic acids (such as hydroxyethyl imino diacetic acid, nitrilo triacetic acid, ethylene diamine tetraacetic acid, hydroxyethyl ethylenediamine triacetic acid, and diethylene triamine pentacetic acid), alpha-hydroxy acids (such as citric acid, tartaric acid, and gluconic acid), and condensed phosphates and phosphonates. The preferred chelating agents for use in the present invention are ethylenediamine tetraacetic acid and pharmaceutically-acceptable salts thereof, especially sodium ethylenediamine tetracetate. Other useful calcium chelating components include ethane-1-hydroxy-1,1-diphosphonic acid, methane diphosphonic acid, hydroxy methane disphosphonic acid and mixtures thereof.

Other components conventionally found in contact lens disinfecting and soaking solutions, such as buffers, surfactants and viscosity control agents, may be included in the compositions of the present invention at their artestablished usage levels. Thus, the compositions may optionally contain from about 0.01% to about 5% of a pharmacologically-acceptable buffer. Examples of ophthalmologically-physiologically acceptable buffers which may be used in the present invention include combinations of boric acid and its sodium salt, phosphoric acid and its sodium salts, citric acid and its sodium salts, lactic acid its sodium salt, amino acids (such as glycine or glutamic acid) and their sodium salts, and maleic acid and its sodium salt. Preferred compositions of the present invention may additionally contain from about 0.01% to about 5% of a pharmacologically-acceptable viscosity control agent, such as polyvinyl alcohol, methyl cellulose, hydroxyethyl cellulose, hydroxypropyl cellulose, soluble polyhydroxyethyl methacrylate (known as poly hema), polyvinyl pyrollidone, and mixtures thereof.

The solutions of the present invention may also contain from about 0.01% to about 5% of a pharmacologically- and ophthalmologically-acceptable surfactant, particularly a nonionic surfactant. These surfactants are especially useful when the solutions are formulated to clean the lenses as well as to sterilize them. The surfactants which may be employed in the present invention must be completely miscible with water at the concentrations employed and must provide a clear solution. In addition, the surfactant must be stable under the disinfecting conditions, must not act adversely with the soft contact lens, nor with other materials present in the solution and, finally, must not irritate the eye. The surfactant preferably is not absorbed by the soft contact lens material, while being capable of solublizing the proteinaceous and lipid materials adsorbed onto the lens and, further, preventing redeposition during sterilization and subsequent storage. Useful nonionic surfactants are well-known in the art and include, but are not limited to, hydroxyalkylated and polyoxyalkylated surfactants, such as n-hydroxyalkylated carboxamides of fatty acids of from 10 to 18 carbon atoms, preferably of from 12 to 14 carbon atoms, and having 0 or 1 sites of olefinic unsaturation as the only unsaturation, preferably being saturated. These compounds will normally contain two hydroxyalkyl groups of from 2 to 3 carbon atoms which may be the same or different.

The polyoxyalkylated nonionic surfactants may be solely comprised of ethoxy or propoxy groups or may have a polyoxyalkylene chain bonded directly or indirectly to an aliphatic chain of from 10 to 18 carbon atoms. The alkylcontaining group may be a sorbitan ester, an alkylphenyl, alkyl, carboxylic acid, or the like. The polyoxyalkylene chain may be a homo-oligomer or co-oligomer, with the homo-oligomer normally being ethyleneoxy groups and the co-oligomer being a random or block co-oligomer of ethyleneoxy and propyleneoxy groups. These various nonionic detergents are commercially available under a wide variety of tradenames, such as Tween, Igepal, Pluronic, Brij, and Myrj. The alkyleneoxy chains will generally range on the average of from about 5 to about 60 oxyalkylene units. Ampholytic surfactants, such as betaines having an aliphatic carbon chain bonded to nitrogen of from about 10 to 18 carbon atoms, preferably from about 10 to 14 carbon atoms, may also be used herein. Particularly preferred surfactants for use in the present invention include polyoxyethylenes, octylphenoxy polyethoxy ethanols, polysorbates and mixtures thereof.

The present invention also encompasses a method for cleaning and disinfecting hydrophilic soft contact lenses wherein the lenses are contacted with a safe and effective amount of the $C_5$–$C_{12}$ fatty acids. In practicing this method, the fatty acids will generally be in the form of an aqueous solution having a concentration of from about 1 to about 200, preferably from about 1 to about 175, millimoles of a mixture of the free fatty acid and the carboxylate (anionic) salt per liter. The microbiocidal activity of the $C_5$–$C_{12}$ carboxylate antimicrobials used herein is directly related to the presence of their respective free acids in solution. The concentration of free carboxylic acid in solution, as opposed to carboxylate salt (anionic) form, is a function of the pH of the solution. The carboxylic acid salts can be used herein, but only as long as the pH of the solution is in the acid range so that the minimum lethal concentration (MLC) of free acid is present. Accordingly, the amount of acid or acid salt used will vary somewhat with the pH. The amount of a given acid salt or acid which will provide the MLC at a given pH will depend on the pKa of the acid. Of course, knowing the pKa, the MLC of the particular acid and the solution pH, the amount of any $C_5$–$C_{12}$ acid or acid salt to be used is easily calculated. Representative MLC values are as follows: $C_5$ (0.11 M); $C_6$ (30 mM); $C_7$ (9 mM); $C_8$ (3 mM); and $C_9$ (1 mM). The compositions, described above, are preferred for use in this method. Generally, the contact lenses are contacted with the fatty acid components for periods ranging between about 5 minutes and about 12 hours, although under some circumstances, longer or shorter periods may be utilized.

The following non-limiting examples illustrate the compositions and the methods of the present invention.

EXAMPLE I

A disinfecting solution for hydrophilic contact lenses of the present invention, having the formula given below, was formulated in the following manner.

| | |
|---|---|
| Octanoic acid concentration | 40 mM |
| pH | 6.0 |
| Sodium chloride | 32 mM |
| Ethylene diamine tetraacetic acid, disodium salt | 0.1% |
| Monobasic sodium phosphate | 50.4 mM |
| Dibasic sodium phosphate | 4.6 mM |

The following quantities of materials were measured out and added to a 100 milliliter volumetric flask: 0.943 grams of sodium octanoate; 0.696 grams of monobasic sodium phosphate; 0.123 grams of dibasic sodium phosphate; 0.1 gram ethylenediamine tetraacetic acid, disodium salt; and 0.187 grams of sodium chloride. These materials were dissolved in 100 milliliters of distilled water. The resulting solution had a pH of 6.0 when measured at a temperature of 23° C.

Compositions of the present invention may also be formulated by adding about 0.5% of a surfactant selected from polyoxyethylene, polysorbate 80, octylphenoxy (oxyethylene) ethanol,, and mixtures thereof to the composition described above. A viscosity control agent selected from polyvinyl alcohol, methyl cellulose, hydroxyethyl cellulose, hydroxypropyl cellulose, soluble poly hema, polyvinyl pyrollidone, and mixtures thereof may also be added to the formulation given above at a level of about 0.5%.

Compositions of the present invention may also be formulated by replacing the sodium octanoate, in the compositions described above, with an equivalent amount of a fatty acid selected from sodium pentanoate, sodium pentanoate, sodium hexanoate, sodium heptanoate, sodium nonanoate, sodium decanoate, sodium undecanoate, or sodium dodecanaote.

EXAMPLE II

The level of octanoate absorbed by Bausch & Lomb Soflens contact lenses from disinfecting solutions of the present invention, as well as the rate at which the octanoate is desorbed from the lenses was determined by the procedure described below.

The test solution used in this procedure was that described in Example I, except that the sodium octanoate was labeled using carbon-14, having a radiochemical purity of greater than 98.5%, a chemical purity of greater than 99%, and a specific activity of 164 mCi/gram. 35 Milliliters of the test solution was prepared. Four scintillation vials were filled with 5.03±0.03 milliliters of this solution. Another four vials were filled with 2.51±0.03 milliliters of the solution. Two vials from each set of four vials were set aside for radioassay. The remaining four vials each had a contact lens (Bausch & Lomb Soflens) submersed in it. After 4 hours, each lens was removed from its vial with fine forceps. The lenses were gently touched to the inside walls of the vial to remove excess fluid and were not rinsed. The lenses were then immediately transferred to vials containing 2.5 milliliters of a 0.9% sodium chloride solution and gently swirled.

After 15 seconds, the lenses were again transferred to another set of vials containing 2.5 milliliters of 0.9% sodium chloride solution. This process was repeated according to the lens transfer schedule specified below.

| Vial Sequence | Process | Vial Content | Submersion Time |
|---|---|---|---|
| First | Sorption | Octanoate Solution (Ex. I) | 4 hours |
| Second | Desorption | 0.9% NaCl | 15 seconds |
| Third | Desorption | 0.9% NaCl | 15 seconds |
| Fourth | Desorption | 0.9% NaCl | 30 seconds |
| Fifth | Desorption | 0.9% NaCl | 1 minute |
| Sixth | Desorption | 0.9% NaCl | 3 minutes |
| Seventh | Desorption | 0.9% NaCl | 5 minutes |
| Eighth | Desorption | 0.9% NaCl | 15 minutes |
| Ninth | Desorption | 0.9% NaCl | 35 minutes |

All vials utilized in this process were submitted for radioassay. Two unused 2.5 milliliter samples of the 0.9% sodium chloride solution were also submitted for radioassay. The lenses were retained in the vials of the final transfer and were submitted for radioassay.

If the sum of the radioactivity from the desorption vials (saline solutions) plus the initial sorption vial (C-14 octanoic acid solution) did not add up to at least 95% of the radioactivity of the unused $C_{14}$ octanoic acid vials, then an additional transfer of the lens was performed within a week of the beginning of the experiment. The vial used for lens storage up to that time was then submitted for radioassay. If this radioactivity did not bring the total radioactivity up to at least 95% recovery, then the lens used for that sequence of transfer was submitted in the storage vial containing 2.5 milliliters of 0.9% sodium chloride. If submission of the lenses was not required for radioactivity balance data, the lenses were submitted for radioassay to demonstrate negligible radioactivity remaining in them.

The procedure above was repeated on four samples and the results were averaged over these four runs. The average percent sodium carbon-14 octanoate remaining in the contact lens material as a function of desorption time is summarized in the table below.

Average sodium octanoate absorbed per lens=0.546 mg ±0.031 mg

| | Desorption of Sodium Octanoate | |
|---|---|---|
| Desorption Interval | Cumulative Desorption Time (min) | % ($NaC^{14}$-Octanoate) Remaining |
| 15 seconds | 0.25 | 70.6 |
| 15 seconds | 0.50 | 58.2 |
| 30 seconds | 1.0 | 44.1 |
| 1 minute | 2.0 | 30.4 |
| 3 minute | 5.0 | 14.8 |
| 5 minute | 10.0 | 5.7 |
| 15 minute | 25.0 | 1.0 |
| 35 minute | 60.0 | 0.5 |

These data indicate a very rapid and complete desorption of the sodium octanoate material from the contact lenses. Radioassay of selected lenses showed less than 2 μg/lens remaining in each lens plus its storage vial. This is not considered to constitute significant accumulation since less than 2 μg/lens is the approximate level of the serially-diluted background caused by transfer of moisture with transfer of the lenses. Further, repetition of the absorption/desorption experiment, described above, using the same lenses had no accumulative effect. These results are particularly significant when compared with similar data relating to the desorption of chlorhexidine from Bausch & Lomb soft contact lenses summarized in the following table. This information was obtained from Richardson, et al., *J. Pharm. Pharmac.*, 30, 469–475 (1978), see especially Table 4.

| Desorption of Chlorhexidine Gluconate from Saturated Poly HEMA Lenses | | |
|---|---|---|
| Cumulative Desorption Interval (days) | mg. Released per day | % Remaining (cumulative) |
| 1 | 0.060 | 90 |
| 2 | 0.005 | 89 |
| 3 | 0.029 | 84 |
| 4 | 0.046 | 76 |
| 5 | 0.081 | 62 |
| 6 | 0.024 | 58 |

EXAMPLE III

Using a procedure similar to that described in Example II and the composition described in Example I, the desorption characteristics of a composition of the present invention were determined using a variety of hydrophilic soft contact lens materials. The lenses tested were Soflens made from a Polymacon polymer; Hydron made from a Polymacon polymer; Durasoft, made from Phemfilcon A polymer; AO Soft made from Tetrafilcon A polymer; and Hydrocurve II, made from Bufilcon A polymer.

The sorption and desorption procedures described in Example II were followed in the present test, except for the Bausch & Lomb Soflens soft contact lenses. Six of the Bausch & Lomb lenses were tested. Two lenses were tested following the usual procedure, except that the lens transfer schedule was not followed; these two lenses were instead desorbed with the following transfer schedule: 5 minutes, 5 minutes, 10 minutes, and 30 minutes. Another pair of soft lenses spent seven days in the sorption vial rather than only four hours. After seven days, these lenses were desorbed according to the usual desorption schedule. The remaining two lenses were placed with test solution in a Bausch & Lomb Lensgard lens carrying case according to the manufacturer's recommended procedures. This was done after the lenses had first soaked for four hours in the test solution. The lenses and solutions in the Lensgard case were subjected to heat sterilization with the Bausch & Lomb Disinfecting Unit II according to the manufacturer's recommended procedures. The unit was allowed to cool and stand overnight and the lenses were desorbed approximately 24 hours after the initial sorption began, using the usual desorption transfer schedule. The test solution was not retained and submitted for radioassay for the final two lenses because of expected evaporative losses in the heat sterilization process. The above treatments were shown to have no significant effect on the time course or completeness of the desorption from the Bausch & Lomb lenses.

The desorption characteristics of the composition of the present invention, tested over a range of soft contact lens materials, is summarized in the following table.

| Lens | Polymer | Total Amount Release μg ± S.D. | % Released at (Minutes) | | |
|---|---|---|---|---|---|
| | | | 1 | 10 | 25 |
| Soflens ® | Polymacon | 558 ± 53(8) | 52 | 90 | 98 |
| Hydron ® | Polymacon | 472 ± 33(2) | 39 | 88 | 97 |
| Durasoft ® | Phemfilcon A | 639 ± 21(2) | 22 | 57 | 82 |
| AO Soft ® | Tetrafilcon A | 536 ± 54(2) | 35 | 76 | 93 |
| Hydrocurve II ® | Bufilcon A | 469 ± 14(2) | 47 | 88 | 98 |

All lenses tested, with the exception of Durasoft, gave a plateau in a desorption curve by the one hour time point showing complete release. Durasoft, a nonpolar acrylic, had slower kinetics resulting in complete release as well. In all cases, the desorption exhibited by the composition of the present invention was both complete and rapid when compared with that of chlorhexidine (as described in Example II), an antimicrobial agent conventionally used in contact lens disinfecting solutions.

Substantially similar results (i.e., results superior to conventional chlorhexidine-containing disinfecting solutions) are obtained when the sodium octanoate used in the above example is replaced, in whole or in part, by an equivalent amount of n-pentanoic acid, n-hexanoic acid, n-heptanoic acid, n-octanoic acid, n-nonanoic acid, n-decanoic acid, n-undecanoic acid, n-dodecanoic acid, the sodium salt of these acids, or mixtures thereof. Similar results are also obtained where the sodium chloride, used to obtain isotonicity in the solution, is replaced in whole or in part with sodium citrate, sodium lactate, sodium phosphate, and mixtures thereof. Substantially similar results are also obtained where the buffer portion of the solution (i.e., the mono- and dibasic sodium phosphate components) are replaced in whole or in part with combinations of boric acid and its sodium salt, citric acid and its sodium salts, lactic acid and its sodium salt, glycine or glutamic acid and their sodium salts, maleic acid and its sodium salt, or mixtures thereof. The ethylene diamine tetraacetic acid, disodium salt, may also be replaced in whole or in part with ethane-1-hydroxy-1,1-diphosphonic acid, methane diphosphonic acid, hydroxymethane diphosphonic acid and mixtures thereof, yielding similar results.

EXAMPLE IV

Using the procedures described in the U.S. Food and Drug Administration, Bureau of Medical Devices' 1980 monograph on class II contact lens product guidelines for contact lens solution testing, the efficacy of a 4 mM octanoic acid solution of the present invention was determined. The solution tested had a pH of 6.0 and contained the following components per 500 ml. of distilled water:

| | |
|---|---|
| 4.715 g. | sodium octanoate |
| 3.480 g. | $NaH_2PO_4 \cdot H_2O$ |
| 0.615 g. | $Na_2HPO_4 \cdot 7H_2O$ |
| 0.500 g. | $Na_2EDTA$ |
| 0.935 g. | sodium chloride |

The antimicrobial efficacy of the composition was expressed in terms of D-values against a range of microorganisms specified by the U.S. FDA as those which a class II contact lens solution should be effective against. A D-value is the time required to kill 90% of a population of microorganisms. In this study the D-value was calculated from the amount of time required for the product to completely kill a population of about $10^5$ organisms/ml. The results of this study are summarized below.

| Microorganism | D-value (Minutes) |
|---|---|
| Pseudomonas aeruginosa, ATCC 15442 | 0.10 |
| Serratia marcescens, ATCC 17917 | 1.00 |
| Staphylococcus epidermidis, ATCC 14041 | 2.30 |
| Candida albicans, ATCC 10231 | <0.03 |
| Aspergillus fumagatis spores, ATCC 10894 | 4.0 |

By way of comparison, a commercial contact lens disinfecting solution sold by Allergan, under the same testing conditions, had D-values greater than 10 minutes against Serratia marcescens and greater than 2 hours against Aspergillus fumagatis spores. Direct efficacy testing of the above solution against contaminated lenses revealed that the lenses were decontaminated in two hours or less, while the commercially-available solutions tested required at least about 4 hours for comparable performance. Moreover, the commercial solutions yielded only a slight or no decrease in the number of viable A. fumagatis spores after a 4 hour exposure. The antibacterial effectiveness of the currently-available soft contact lens cold disinfection solutions, particularly useful for comparison with the test results herein, is described in Sibley, Soft Lens Cold Disinfection Solutions: A Comparative Study, Contact Lens Forum, December, 1981, pages 41 et seq.

Substantially similar results are obtained when the sodium octanoate used in the above example is replaced, in whole or in part, by an equivalent amount of n-pentanoic acid, n-hexanoic acid, n-heptanoic acid, n-octanoic acid, n-nonanoic acid, n-decanoic acid, n-undecanoic acid, n-dodecanoic acid, the sodium salts of these acids, or mixtures thereof. Similar results are also obtained where the sodium chloride, used to obtain isotonicity in the solution, is replaced in whole or in part, with sodium citrate, sodium lactate, sodium phosphate, and mixtures thereof. Substantially similar results are also obtained where the buffer portion of the solution (i.e., the mono- and dibasic sodium phosphate components) are replaced in whole or in part with combinations of boric acid and its sodium salt, citric acid and its sodium salts, lactic acid and its sodium salt, glycine or glutamic acid and their sodium salt, maleic acid and its sodium salt, or mixtures thereof. The ethylene diamine tetraacetic acid, disodium salt, may also be replaced in whole or in part with ethane-1-hydroxy-1,1-diphosphonic acid, methane diphosphonic acid, hydroxymethane diphosphonic acid and mixtures thereof, yielding similar results.

What is claimed is:

1. An aqueous isotonic solution having a pH between about 3.5 and 6.5, suitable for cleaning, disinfecting and storing hydrophilic soft contact lenses, comprising:
   (a) from about 0.001% to about 3% of a fatty acid selected from the group consisting of n-pentanoic acid, n-hexanoic acid, n-heptanoic acid, n-octanoic acid, n-nonanoic acid, n-decanoic acid, n-undecanoic acid, and mixtures thereof;
   (b) a sufficient amount of at least one water-soluble salt, compatible with occular tissue, to provide a solution salt content equivalent to from about 0.5% to about 1.8% sodium chloride;
   (c) from about 0.01% to about 2% of a calcium chelator; and
   (d) the balance water.

2. A composition according to claim 1 wherein the fatty acid is selected from the group consisting of octanoic acid, decanoic acid, and mixtures thereof.

3. A composition according to claim 2 wherein the fatty acid is octanoic acid.

4. A composition according to claim 1 or 2 having a pH of from about 5 to about 6.5.

5. A composition according to claim 4 which contains from about 0.01% to about 1.5% of the fatty acid component.

6. A composition according to claim 5 which contains from about 0.05% to about 1.5% of the calcium chelator component.

7. A composition according to claim 1 or 2 wherein the calcium chelator is selected from the group consisting of ethylenediamine tetraacetic acid, ethane-1-hydroxy-1,1-diphosphonic acid, methane diphosphonic acid, hydroxymethane diphosphonic acid and pharmaceutically-acceptable salts thereof.

8. A composition according to claim 1 which additionally contains from about 0.01% to about 5% of a pharmacologically-acceptable buffer.

9. A composition according to claim 1 which additionally contains from about 0.01% to about 5% of a pharmacologically-acceptable surfactant.

10. A composition according to claim 9 wherein the surfactant is selected from the group consisting of polyoxyethylenes, octylphenoxy polyethoxy ethanols, polysorbates and mixtures thereof.

11. A composition according to claim 1 which additionally contains from about 0.01% to about 5% of a viscosity control agent.

12. A composition according to claim 11 wherein the viscosity control agent is selected from the group consisting of polyvinyl alcohol, methyl cellulose, hydroxyethyl cellulose, hydroxypropyl cellulose, soluble poly hema, polyvinyl pyrollidone, and mixtures thereof.

13. A method for cleaning and disinfecting hydrophilic soft contact lenses comprising contacting said lenses with an aqueous solution of a fatty acid selected from the group consisting of n-pentanoic acid, n-hexanoic acid, n-heptanoic acid, n-octanoic acid, n-nonanoic acid, n-decanoic acid, n-undecanoic acid, and mixtures thereof, wherein the concentration of a mixture of the free-acid form of said fatty acid and the carboxylate form of said fatty acid, in said aqueous solution, is from about 1 to about 200 millimolar.

14. A method according to claim 13 wherein the fatty acid is in an aqueous solution having a pH of from about 3.5 to about 6.5.

15. A method according to claim 14 wherein the fatty acid is selected from the group consisting of octanoic acid, decanoic acid, and mixtures thereof.

16. A method according to claim 15 wherein the aqueous solution has a pH of from about 5 to about 6.5.

17. A method according to claim 16 wherein the fatty acid is octanoic acid.

18. A method according to claim 17 wherein the mixture of free octanoic acid and octanoate is present in a concentration of from about 1 to about 175 millimolar.

19. A method for cleaning and disinfecting hydrophilic soft contact lenses comprising contacting said lenses with a safe and effective amount of a composition according to claim 1.

* * * * *